United States Patent [19]
Richmond

[11] Patent Number: 6,068,617
[45] Date of Patent: *May 30, 2000

[54] NEEDLELESS VALVE FOR USE IN INTRAVENOUS INFUSION

[76] Inventor: Frank M. Richmond, 205 A Grant St., Harvard, Ill. 60033

[*] Notice: This patent issued on a continued prosecution application filed under 37 CFR 1.53(d), and is subject to the twenty year patent term provisions of 35 U.S.C. 154(a)(2).

[21] Appl. No.: 08/814,676

[22] Filed: Mar. 11, 1997

Related U.S. Application Data

[63] Continuation of application No. 08/612,875, Mar. 12, 1996, Pat. No. 5,645,538, which is a continuation-in-part of application No. 08/123,632, Sep. 16, 1993, Pat. No. 5,405,333, which is a continuation-in-part of application No. 07/997,610, Dec. 28, 1992, Pat. No. 5,391,150.

[51] Int. Cl.[7] .................................................... A61M 5/00
[52] U.S. Cl. ........................... 604/255; 604/251; 604/30; 604/153
[58] Field of Search ................................ 604/30, 33, 32, 604/9, 246, 247, 251, 255, 153

[56] References Cited

U.S. PATENT DOCUMENTS

| | | |
|---|---|---|
| 2,299,643 | 10/1942 | Moody . |
| 3,831,629 | 8/1974 | Mackal et al. . |
| 4,000,740 | 1/1977 | Mittleman . |
| 4,059,109 | 11/1977 | Tishchlinger . |
| 4,128,098 | 12/1978 | Bloom et al. . |
| 4,143,853 | 3/1979 | Abramson . |
| 4,158,362 | 6/1979 | Durrett et al. . |
| 4,210,173 | 7/1980 | Choski et al. . |
| 4,222,407 | 9/1980 | Roschke et al. . |
| 4,244,445 | 1/1981 | Brignola . |
| 4,274,445 | 6/1981 | Cooper . |
| 4,310,017 | 1/1982 | Raines . |
| 4,311,137 | 1/1982 | Gerard . |
| 4,354,492 | 10/1982 | McPhee . |
| 4,364,387 | 12/1982 | Larkin . |

(List continued on next page.)

*Primary Examiner*—Wynn Wood Coggins
*Assistant Examiner*—Jennifer R. Sadula
*Attorney, Agent, or Firm*—Fitch, Even, Tabin & Flannery

[57] ABSTRACT

An IV port body defining an IV port includes a valve body configured as a luer fitting, and a movable valve member defining an outer periphery that is uninterrupted within the periphery is disposed in the valve body. The valve member is biased to a first configuration, wherein a passageway for fluid communication is not established through the valve body. Also, the valve member can be moved to a second configuration, wherein fluid communication through the body is permitted.

13 Claims, 13 Drawing Sheets

U.S. PATENT DOCUMENTS

| | | |
|---|---|---|
| 4,387,879 | 6/1983 | Tauschinski . |
| 4,405,316 | 9/1983 | Mittleman . |
| 4,429,856 | 2/1984 | Jackson . |
| 4,498,295 | 2/1985 | Knoos ........................................ 60/517 |
| 4,506,691 | 3/1985 | Tseo . |
| 4,535,820 | 8/1985 | Raines . |
| 4,556,086 | 12/1985 | Raines . |
| 4,610,276 | 9/1986 | Paradis et al. . |
| 4,614,437 | 9/1986 | Buehler . |
| 4,681,132 | 7/1987 | Lardner . |
| 4,683,916 | 6/1988 | Raines . |
| 4,752,292 | 6/1988 | Lopez et al. . |
| 4,765,372 | 8/1988 | Beecher . |
| 4,776,369 | 10/1988 | Lardner et al. . |
| 4,782,841 | 11/1988 | Lopez . |
| 4,816,024 | 3/1989 | Sitar et al. . |
| 4,819,659 | 4/1989 | Sitar . |
| 4,838,875 | 6/1989 | Somon . |
| 4,842,591 | 6/1989 | Luther . |
| 4,874,369 | 10/1989 | Kulle et al. . |
| 4,898,581 | 2/1990 | Iwatschenko . |
| 4,917,668 | 4/1990 | Haindl . |
| 4,940,457 | 7/1990 | Olson ........................................ 604/30 |
| 5,070,905 | 12/1991 | Paradis . |
| 5,071,413 | 12/1991 | Utterberg . |
| 5,085,645 | 2/1992 | Purdy et al. . |
| 5,176,658 | 1/1993 | Ranford ..................................... 604/30 |
| 5,190,067 | 3/1993 | Paradis et al. . |
| 5,201,725 | 4/1993 | Kling . |
| 5,230,706 | 7/1993 | Duguette . |
| 5,232,109 | 8/1993 | Tirrell et al. . |
| 5,242,393 | 9/1993 | Brimhall et al. . |
| 5,251,873 | 11/1993 | Atkinson et al. . |
| 5,269,771 | 12/1993 | Thomas et al. . |
| 5,295,657 | 3/1994 | Atkinson . |
| 5,334,180 | 8/1994 | Adolf et al. . |
| 5,349,984 | 9/1994 | Weinheimer et al. . |
| 5,354,278 | 10/1994 | Kriesel ..................................... 604/132 |
| 5,360,413 | 11/1994 | Leason et al. . |
| 5,383,851 | 1/1995 | McKinnon, Jr. et al. . |
| 5,391,150 | 2/1995 | Richmond ................................ 604/247 |
| 5,405,323 | 4/1995 | Rogers et al. . |
| 5,405,333 | 4/1995 | Richmond ................................ 604/257 |
| 5,433,705 | 6/1995 | Giebel et al. . |
| 5,453,097 | 9/1995 | Paradis ..................................... 604/247 |
| 5,454,805 | 10/1995 | Brony . |
| 5,492,531 | 2/1996 | Post . |
| 5,527,306 | 6/1996 | Haining . |
| 5,620,420 | 4/1997 | Kriesel ..................................... 604/133 |
| 5,642,617 | 7/1997 | Larkin et al. ............................. 60/488 |
| 5,645,538 | 7/1997 | Richmond ................................ 604/256 |
| 5,660,205 | 8/1997 | Epstein ..................................... 604/247 |
| 5,694,686 | 8/1996 | Siegel et al. . |
| 5,735,826 | 4/1998 | Lopez . |

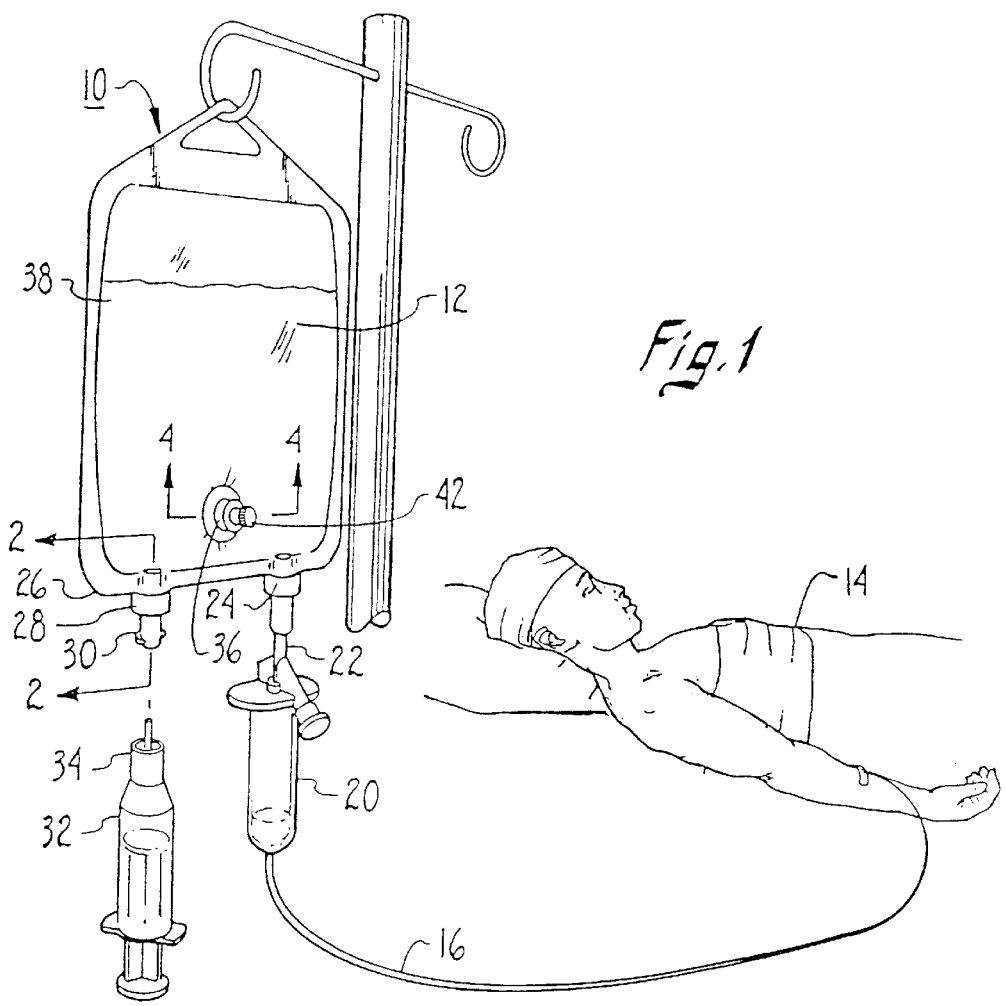
Fig. 1
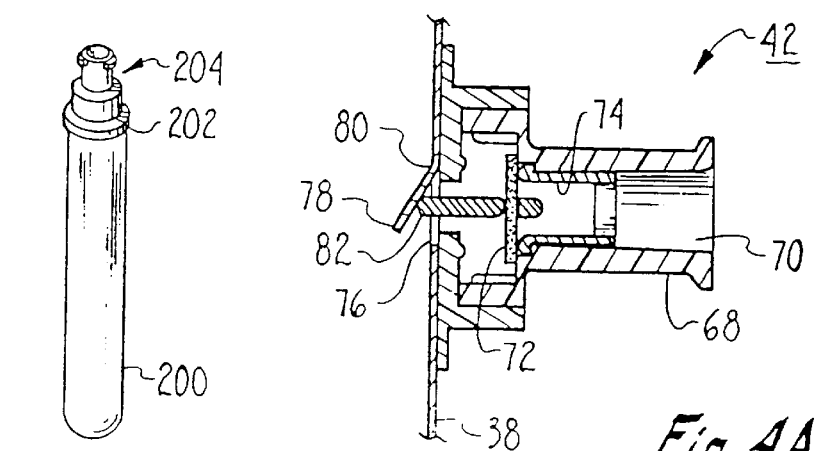
Fig. 1A
Fig. 4A

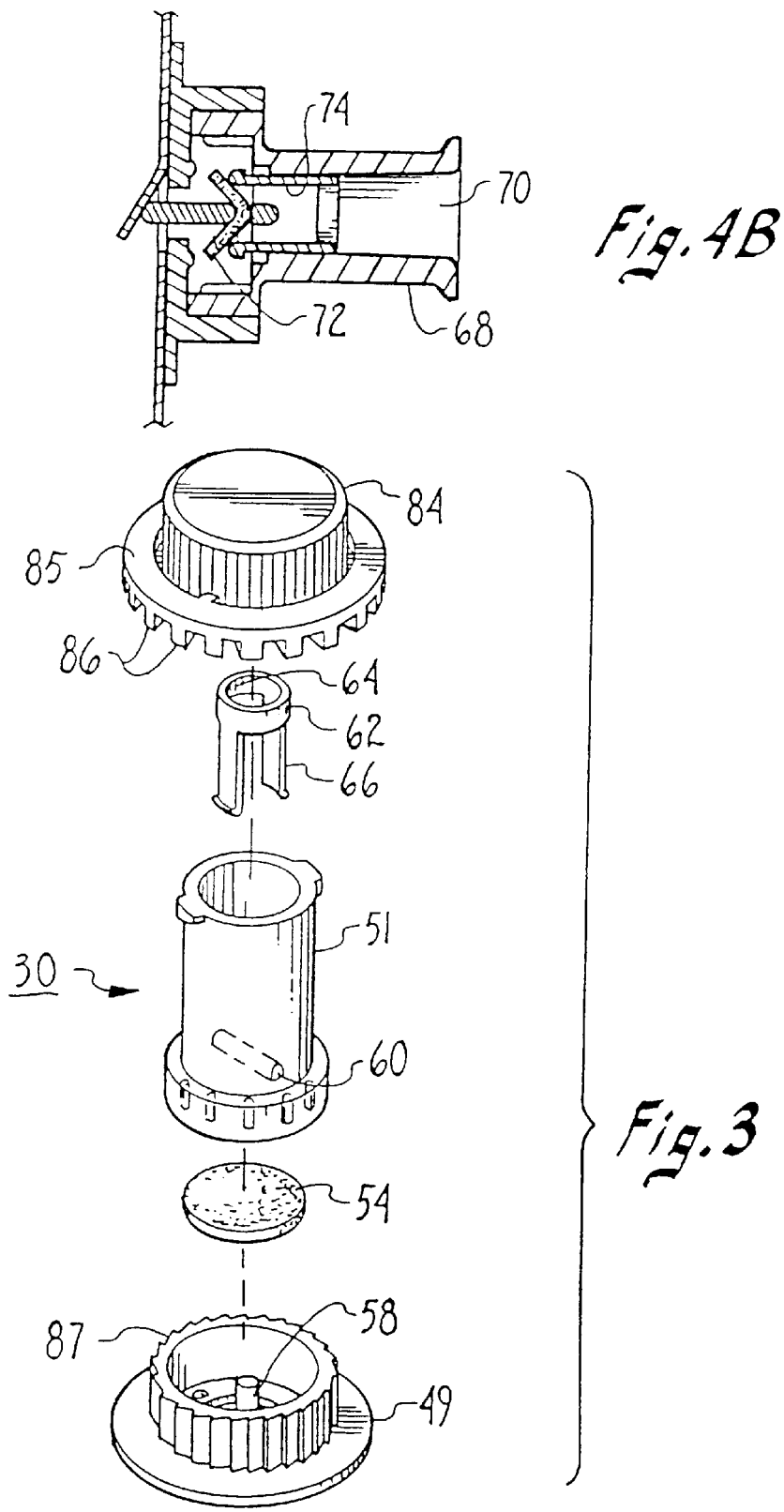

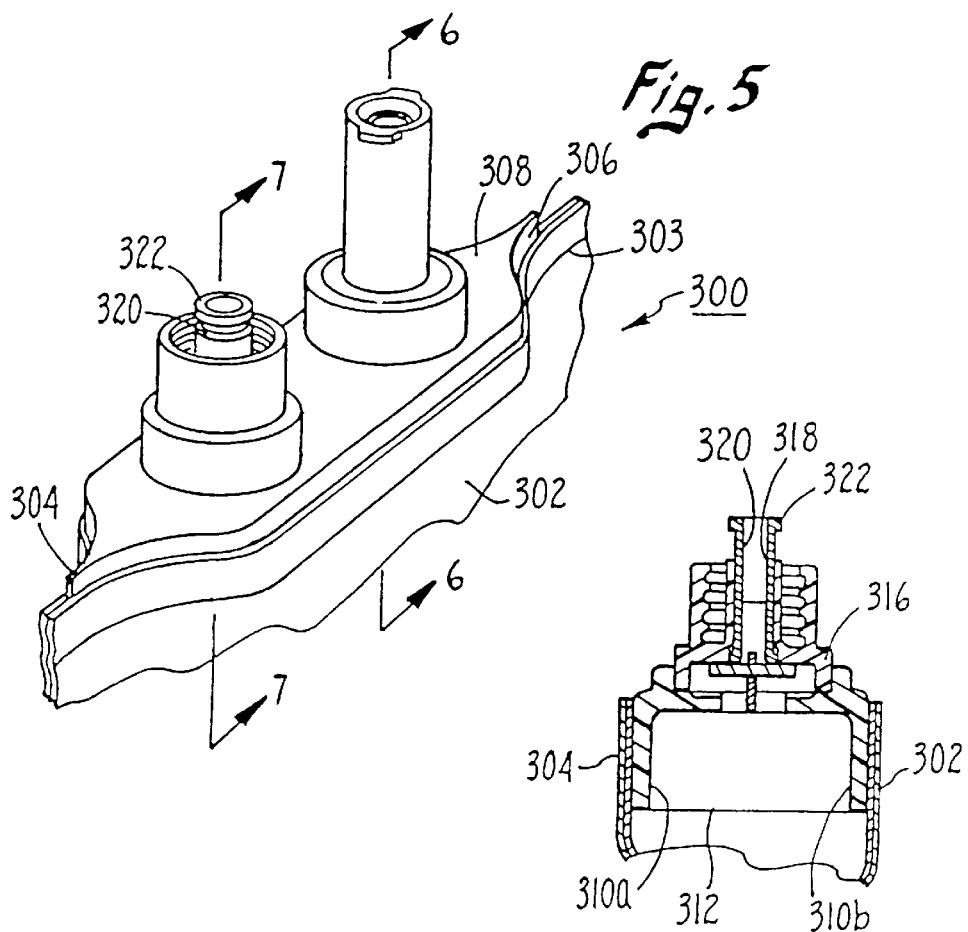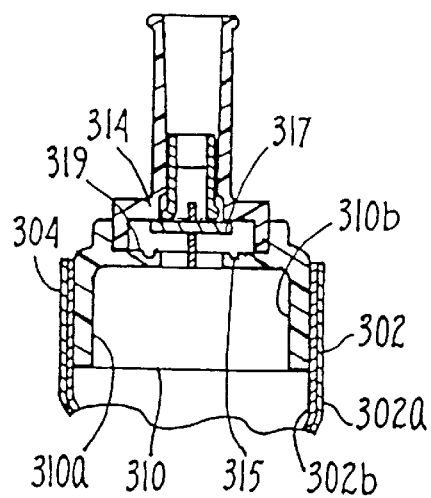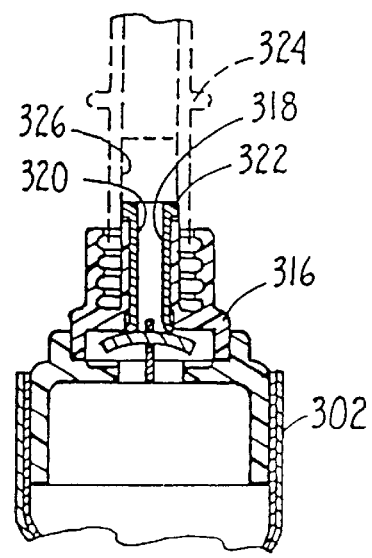

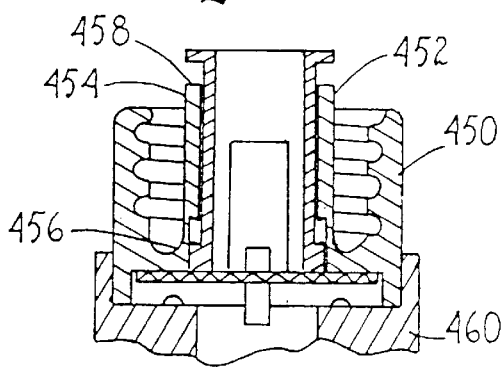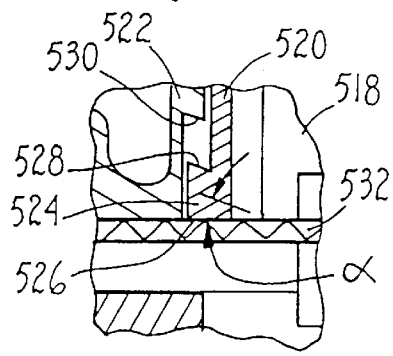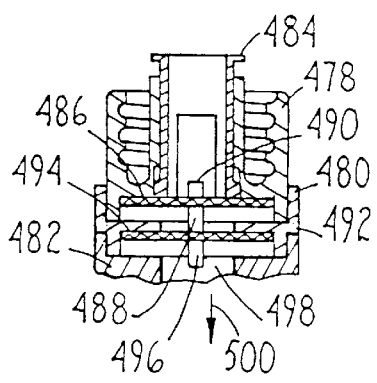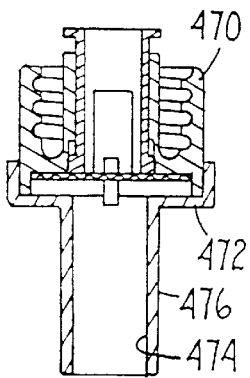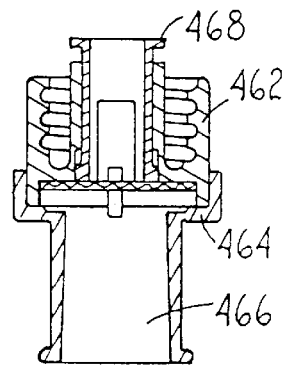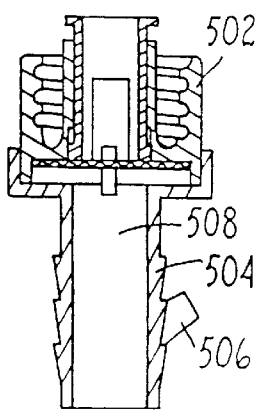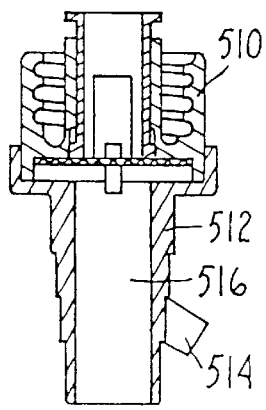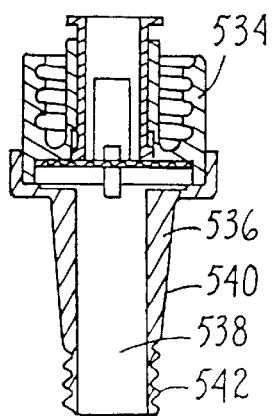

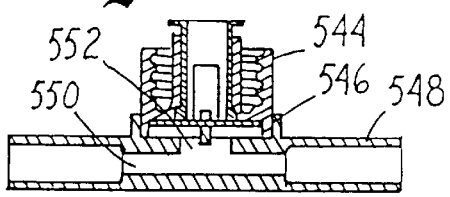
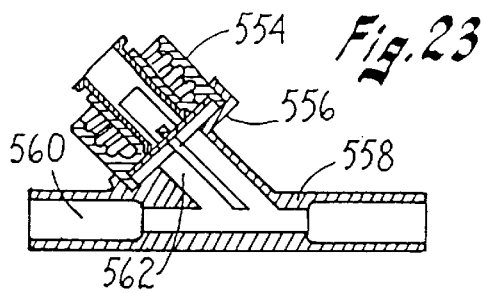
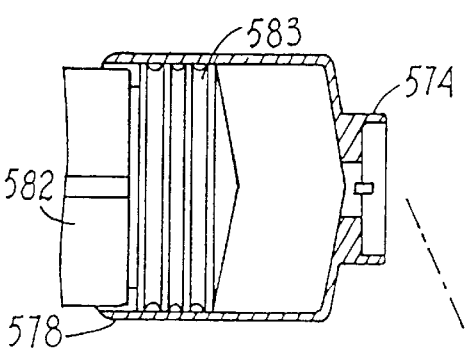
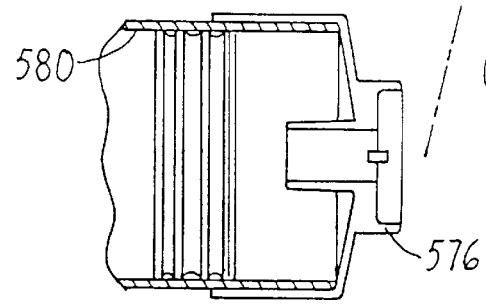
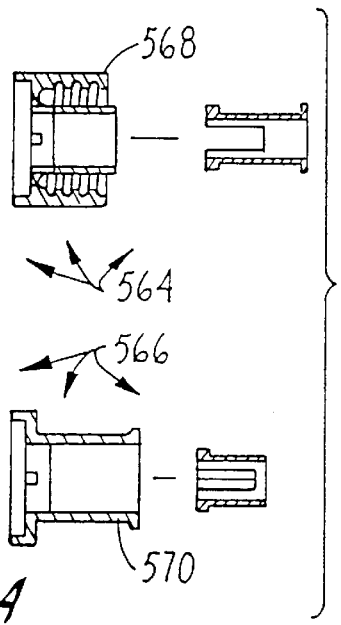
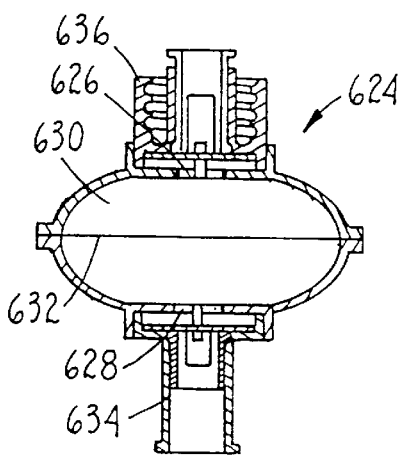
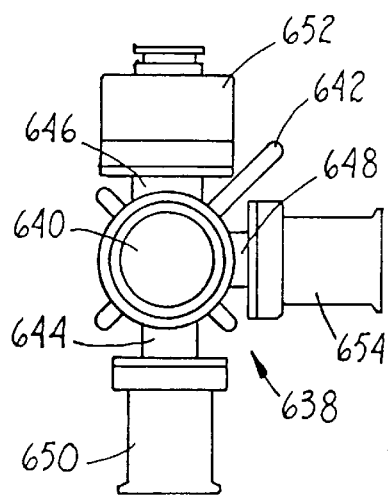

NEEDLELESS VALVE FOR USE IN INTRAVENOUS INFUSION

Related Applications

The present application is a continuation of and claims priority from U.S. patent application Ser, No. 08/612,875, now U.S. Pat. No. 5,645,538, for an invention entitled "Needleless Valve for use in Intravenous Infusion" filed March 12, 1996, which in turn is a continuation-in-part of Ser. No. 08/123,632 U.S. Letters Pat. No. 5,405,333, filed on Sep. 16, 1993 for an invention entitled "Liquid Medicament Bag With Needleless Connector Fitting Using Boat Assembly" which in turn is a continuation-in-part of Ser. 07/997,610 U.S. Pat. No. 5,391,150, filed on Dec. 28, 1992 for an invention entitled "IV Bag With Needleless Connector Ports."

FIELD OF THE INVENTION

The present invention relates generally to intravenous liquid medicament infusion equipment, and more particularly to needleless valves for use therein.

BACKGROUND OF THE INVENTION

One of the most widely used methods of medical therapy is the intravenous (IV) infusion of medicaments and/or nutrients into the bloodstream of a patient. Commonly, syringes or IV containers, such as bags, having at least one opening are used to hold the fluid to be infused. Many IV containers can have more than a single opening, to establish both a pathway for extracting fluid from the container and a pathway for injecting fluid into the container. The openings can be formed in the bottom seam of the container or in the side of the container, and the openings are blocked by membranes.

Ordinarily, to establish fluid flow through the opening the membrane is pierced by inserting a so-called IV spike into the opening. The spike is usually connected to a transparent drip chamber for visually verifying fluid flow and flow rate from the container (e.g., a bag), and the drip chamber in turn is connected to an IV line to the patient. Alternatively, a resealable membrane can cover one of the openings, and the resealable membrane can be punctured by the needle of a syringe to inject additional fluid from the syringe into the bag.

It has become apparent, however, that the use of "sharps" such as needles and spikes raises the possibility that a health care worker could inadvertently puncture the container/bag or himself with the needle or spike, and thus increase the risk of transmitting tragic diseases such as AIDS. Thus, the use of needles and other "sharps" should be avoided whenever possible in the health care environment.

Further, even though a spike may not necessarily be considered a "sharp" under all circumstances, the existing membrane arrangements requiring the use of a spike do not permit removal of the spike from the container (bag) until the contents of the bag are completely exhausted. This is because the hole a spike makes in a membrane is typically too large to permit the membrane to reseal. Thus, once inserted, a spike is not usually removed from an IV bag until the bag is empty, which can understandably limit use of the bag and its contents.

Accordingly, it is an object of the present invention to provide a needleless valve for use with IV components. Another object of the present invention is to provide a spikeless/needleless valve in combination with various IV components and configurations. Yet another object of the present invention is to provide a spikeless/needleless IV valve that is easy to use and cost-effective to manufacture.

SUMMARY OF THE INVENTION

A device for holding liquid medicament includes an IV component having an opening formed therein. A valve including a valve body is operably engaged with the opening, and the valve has a first position, wherein a passageway for fluid communication is established through the opening, and a second position, wherein fluid communication through the opening is not permitted. In accordance with the present invention, the valve includes a male valve element having a skirt disposed within the valve body and an engagement surface extending outwardly beyond the valve body for contacting a spikeless/needleless connector to cause the valve element to reciprocate relative to the IV component. The valve is biased to the second position and is engageable with the spikeless/needleless connector to establish the first position of the valve.

Preferably, the IV component is a component selected from the group of components consisting of: IV containers and bags, syringes, spikes, fluid lines, drip chambers, connector fittings, filters, Burette chambers, stopcocks, and multiport valves.

In another aspect of the present invention, a valve includes a hollow body defining a fluid passageway therethrough, and a resilient valve disc is positioned in the fluid passageway. The disc is biased to a closed configuration, wherein the disc blocks fluid flow through the fluid passageway, and the disc is movable to an open configuration, wherein fluid flow is permitted through the fluid passageway. Further, the valve includes a male valve element which is formed with a skirt and an engagement surface extending outwardly from the fluid passageway for contacting a spikeless/needleless connector. The spikeless/needleless connector can be advanced against the valve element to urge the valve element against the valve disc and thereby move the valve disc to the open configuration.

These and other aspects of the present invention can best be appreciated in reference to the accompanying drawings in which like numerals refer to like parts, and in which:

BRIEF DESCRIPTION OF THE DRAWINGS

FIG. 1 is a perspective view of the IV bag of the present invention, shown in one intended environment;

FIG. 1A is a perspective view of a glass vial with reflex valve;

FIG. 3 is an exploded view of the valve shown in FIG. 2A, with portions of the tamper-proof cap broken away, or shown in phantom for clarity;

FIG. 4A is a cross-sectional view of another one of the valves of the IV bag, as seen along the line 2—2 in FIG. 1, with the valve in the closed position;

FIG. 4B is a cross-sectional view as would seen along the line 2—2 in FIG. 1, with the valve in the open position;

FIG. 5 is a perspective view of a liquid medicament bag having a male and a female reflex valve, with portions of the bag broken away;

FIG. 6 is a cross-sectional view of the liquid medicament bag of the present invention, as seen along the line 6—6 in FIG. 5;

FIG. 7 is a cross-sectional view of the liquid medicament bag of the present invention, as seen along the line 7—7 in FIG. 5, with the valve in the closed configuration;

FIG. 8 is a cross-sectional view of the liquid medicament bag of the present invention, as would be seen along the line 7—7 in FIG. 5, with a female luer fitting shown in phantom engaging the valve, with the valve in the open configuration;

FIG. 14 is a cross-sectional view of a male reflux valve of the present invention shown disposed in a male Luer fitting, with portions broken away for clarity;

FIG. 15 is a cross-sectional view of a male reflux valve disposed in a male Luer fitting which has been coaxially bonded to a female Luer fitting;

FIG. 16 is a cross-sectional view of a male Luer fitting with male reflux valve bonded to an annular fitting;

FIG. 17 is a cross-sectional view of a male Luer fitting with male reflux valve in combination with a check valve;

FIG. 18 is a cross-sectional view of a male Luer fitting with male reflux valve bonded to a barbed connector;

FIG. 19 is a cross-sectional view of a male Luer fitting with male reflux valve bonded to a stepped connector;

FIG. 20 is an enlarged cross-sectional view showing a valve element of the present invention having an angled contact surface;

FIG. 21 is a cross-sectional view of a male Luer fitting with male reflux valve bonded to a threaded connector;

FIG. 22 is a cross-sectional view of a male Luer fitting with male reflux valve bonded to a "T"-site connector;

FIG. 23 is a cross-sectional view of a male Luer fitting with male reflux valve bonded to a "Y"-site connector;

FIG. 24 is an exploded cross-sectional view showing a male Luer fitting and male reflux valve and a female Luer fitting with female reflux valve in combination with two types of syringes;

FIG. 26 is a cross-sectional view of a male Luer fitting with male reflux valve and female Luer fitting with female reflux valve bonded to a Burette chamber;

FIG. 27 is a plan view of a plurality of Luer fittings with reflux valves operably engaged with a stopcock;

DESCRIPTION OF THE PREFERRED EMBODIMENT

Figure 2A:
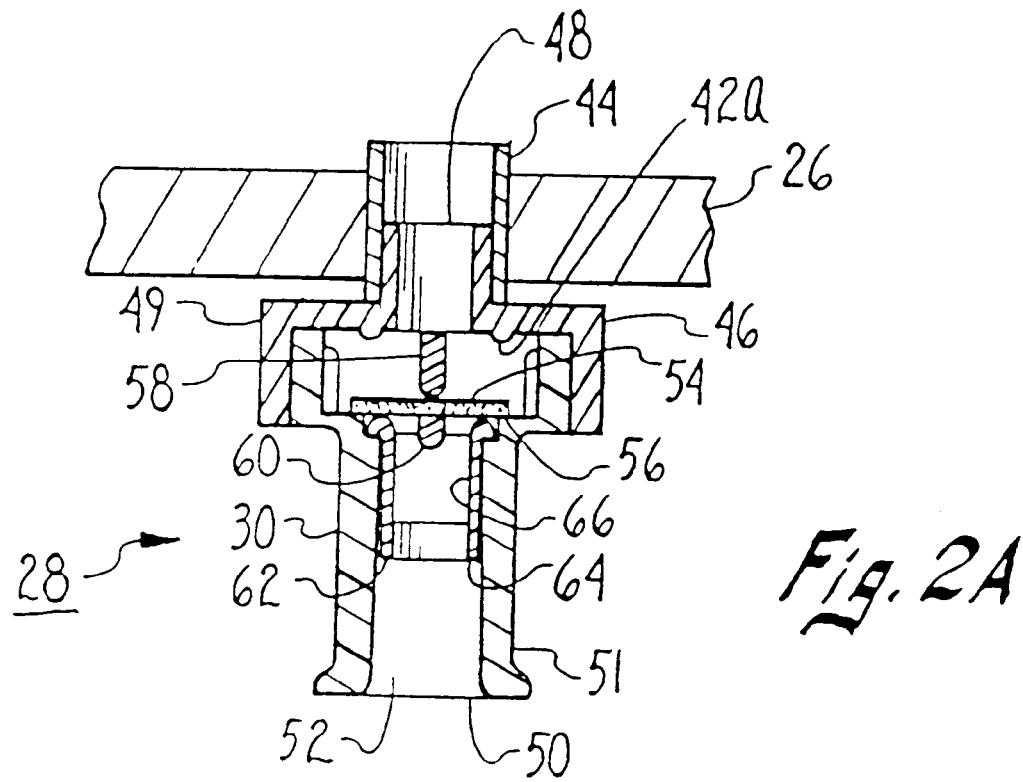
FIG. 2A is a cross-sectional view of one of the valves of the IV bag, as seen along the line 2—2 in FIG. 1, with the valve in the closed position.

Referring initially to FIG. 1, an intravenous (IV) infusion container, configured for purposes of disclosure as a bag, is shown and generally designated 10. Preferably the bag 10 is made of a suitable inert, biocompatible, flexible material, such as polyvinylchloride (PVC) or plex dr. It is to be understood, however, that the principles of the present invention can be applied to other types of IV fluid containers, such as semi-rigid containers (not shown), multi-layer bags for holding cell culture (FIG. 6), or glass bottles and vials (FIG. 5).

As shown in FIG. 1, the bag 10 holds a fluid 12 to be infused into a patient 14 through IV line 16. It is to be understood that the IV line 16 may be operably engaged with respective devices, such as roller clamps (not shown) for selectively permitting fluid communication through the IV line 16.

FIG. 1 shows that the IV line 16 is connected to a conventional drip chamber 20, and the drip chamber 20 is in turn connected to a conventional spike 22. The spike 22 is engaged with a conventional port 24 of the bag 10. As shown in FIG. 1, the port 24 is essentially a tube that has a first end inserted into an opening in the IV bag 10 at the bottom seam 26 of the IV bag 10. The conventional port 24 has a membrane (not shown) positioned therein, and the spike 22 pierces the membrane to establish a path for fluid communication between the spike and the interior of the IV bag.

Still referring to FIG. 1, the bag 10 also has a spikeless/needleless port 28 that includes a tube which is inserted into an opening in the bottom seam 26 of the bag 10 and then bonded by means well-known in the art (e.g., ultra-sonic welding, solvent bonding, heat staking, spin welding or rf sealing). Alternatively, the tube of the port 28 can be formed integrally with the IV bag 10, or the tube can be bonded internally to the bag 10.

FIG. 1 further shows that the port 28 includes a valve 30 which is configured as a female luer fitting. A needleless syringe 32 can be operably engaged with the spikeless/needleless port 28. Preferably, the needleless syringe 32 has an end 34 configured as a male luer fitting, to facilitate engagement of the syringe 32 with the spikeless/needleless port 28. The syringe 32 can be used to inject additional fluid into the bag 10. Alternatively, a blunt spike (not shown) having an end configured as a male luer fitting can be engaged with the spikeless/needleless port 28 to establish a passageway for fluid infusion from the bag 10 into an IV line (not shown) and thence into the patient 14.

While FIG. 1 shows a spikeless/needleless port 28 and a conventional port 24, it is to be understood that additional spikeless/needleless ports (not shown) can be included in the bag 10. It is to be further understood that the conventional port 24 can be omitted from the bag 10, or additional conventional ports Knot shown) included in the bag 10. In any case, the ports 24, 28 that extend from the bottom seam 26 of the bag 10 can be formed integrally with the bag 10 or attached to the bag 10 by well-known means, e.g., by rf sealing, ultrasonic welding, heat staking, spin welding, or solvent bonding.

In addition to the ports 24, 28 that extend from the bottom seam 26 of the bag 10, FIG. 1 shows that another port 36, colloquially known as a "belly button," can be formed in a side surface 38 of the bag 10. Preferably, the belly button port 36 incudes an opening in the side surface 38 of the bag 10, and a valve 42 is disposed in the opening. A needleless syringe (not shown), e.g., a syringe having a male luer fitting in lieu of a sharp needle, can be engaged with the belly button port 36 to inject or extract fluid from the bag 10.

Now referring to FIG. 2A, the details of the spikeless/needleless port 28 can be seen. As shown, the spikeless/needleless port 28 includes a hollow tube 44, and the valve 30 is positioned in the tube 44 to selectively prevent fluid communication through the tube 44. The valve 30 includes a rigid, preferably plastic (e.g., PVC) valve body 46 that has a fluid inlet 48, a fluid outlet 50, and a fluid passageway 52 formed in the valve body 46 between the inlet 48 and outlet 50. The valve body 46 can be a unitary structure, or be made of two or more pieces that are bonded together, as shown. For example, the inlet 48 can be formed from a first piece 49, the outlet 50 can be formed from a second piece 51, and the two pieces can be bonded together by means well-known in the art, e.g., solvent bonding, ultrasonic sealing, or rf welding.

In cross-reference to FIGS. 2A and 3, the valve 30 also includes valve member 54 that is disposed in the fluid passageway 52. Specifically, the periphery of the valve member 54 rests on a seating surface 56 of the valve body 46 to establish a fluid-tight seal between the valve member 54 and seating surface 46. In other words, the valve member 54 is biased to the closed configuration shown in FIG. 2A. A support element 58 is formed in the fluid passageway 52 and extends across the fluid passageway 52.

The support element 58 supports the valve member 54 in the center thereof. To this end, a slight depression may be formed in the center of the valve member 54 to receive the support element 58 and thereby prevent side-to-side motion of the valve member 54 relative to the support element 58. As shown, the support element 58 is shaped as a cylinder, but it is to be understood that the support element 58 can have other suitable shapes, e.g., the support element 58 can have a triangular shape.

Additionally, a retainer element 60 is formed on the valve body 46 and extends across the fluid passageway 52. As shown, the retainer element 60 is positioned on the valve body 46 on the opposite side of the valve member 54 from the support element 58. Accordingly, the retainer element 60 holds the center of the valve member 54 against the support element 58.

Still referring to FIGS. 2A and 3, a rigid urging member 62 is shown slidably disposed in the fluid passageway 52 for reciprocal movement therein. As shown, the urging member 62 has an annular head 64 and a skirt 66 that depends from the head 64. As further shown, the skirt 66 includes a plurality of, preferably two, legs. The urging member 62 can be forced against the valve member 54 by advancing an appropriate connector fitting (not shown), such as a male luer fitting, into the fluid passageway 52 and against the urging member 62.

Figure 2B:
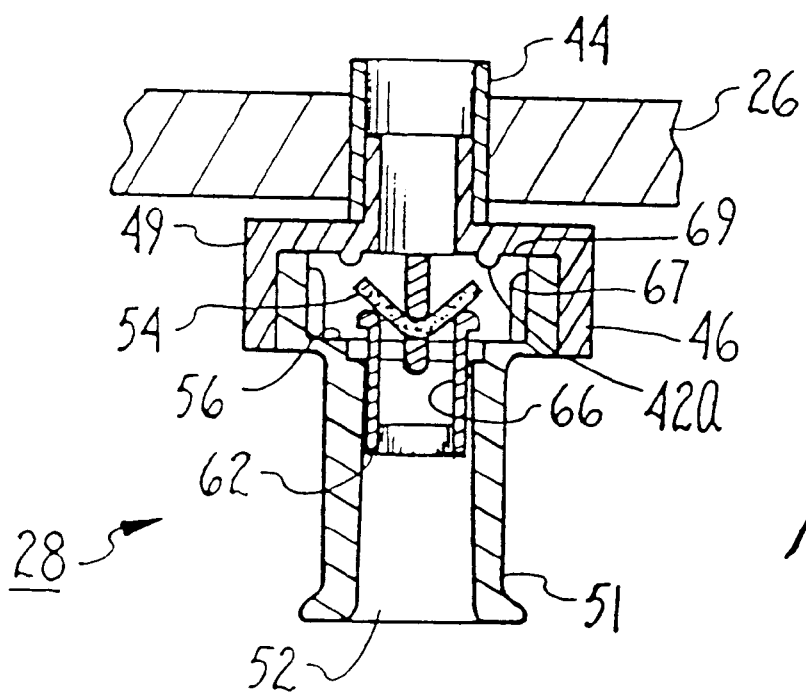
FIG. 2B is a cross-sectional view of one of the valves of the IV bag, as would be seen along the line 2—2 in FIG. 1, with the valve in the open position.

As shown in FIG. 2B, when the urging member 62 is forced against the valve member 54, the skirt 66 of the urging member 62 contacts the surface of the valve member 54. This deforms the valve member 54, causing the sealing surface of the valve member 54 to be distanced from the seating surface 56 of the valve body 46, and thereby permitting fluid communication through the fluid passageway 52. Stated differently, a spikeless/needleless connector can be advanced into the fluid passageway 52 to force the urging member 62 against the valve member 54 and deform the valve member 54 into an open configuration. When the spikeless/needleless connector is retracted from the fluid passageway 52, the resiliency of the valve member 54 causes the valve member 54 to resume its normally closed configuration, shown in FIG. 2A.

Referring back to FIG. 3, a tamper-resistant cap 84 can be engaged with the valve 30. In one presently preferred embodiment, a skirt 85 of the cap 84 has a plurality of resilient ratchet threads 86. The ratchet threads 86 are configured generally as right triangles, as shown, and permit rotation of the cap 84 in the clockwise direction relative to the valve 30 to thereby engage the cap 84 with the valve 30. The threads 86 do not, however, permit easy rotation of the cap 84 in the counter clockwise direction. The threads 86 ratchetably engage blades 87 that are formed on the first piece 49. It is to be understood that the cap 84 can engage any appropriate surface of the first piece 49 or other appropriate surface of the valve 30.

FIGS. 4A and 4B show that the valve 42 is, in all essential respects, identical to the valve 30. Specifically, the valve 42 has a valve body 68 forming a fluid passageway 70. A valve member 72 is positioned in the fluid passageway 70 for selectively blocking fluid communication therethrough. An urging member 74 is disposed in the fluid passageway 70 for reciprocal movement therein, and a spikeless/needleless connector (not shown) can be advanced into the fluid passageway 70 against the urging member 74 to open the valve 42.

Cylindrical or pyramidal protrusions 42a can be formed on the valve 42 for preventing a vacuum lock between the valve member 118 and the first flange 40. Alternatively, grooves (not shown) could be formed in the valve body 68 for preventing a vacuum lock between the valve member 72 and the valve body 68.

The valve 42 is attached, as by solvent bonding, spin welding, rf welding, or ultrasonic sealing, to the side 38 of the bag 10. An opening 76 is formed in the side 38 of the bag 10, for establishing a pathway for fluid communication into and out of the bag 10. Alternatively, an opening (not shown) can be formed in the top or bottom seam of the bag 10, and additional openings (not shown) can be formed in the bag 10.

The opening 76 can be formed in the side 38 of the bag 10 during manufacture of the bag 10 by cutting out a portion of the bag 10. More preferably, a die cut is made in the side 38 of the bag 10 in a partially circular pattern to form a flap 78. The flap 78 remains attached to the bag 10 by an uncut nick 80, and a protrusion 82 is formed on the valve 42 for urging against the flap 78 to unblock the opening 76 when the valve 42 is attached to the bag 10. Thereby, the flap 78 does not prevent fluid flow through the opening 76, once the valve 42 is in place, and the flap 78 does not become detached from the bag 10. This ensures that the flap 78 will not enter the fluid in the bag 10 and thus will not foul any of the IV components valve member discussed above. Alternatively, the flap 78 can be separated from the bag 10 during manufacturing, and the protrusion 82 omitted from the valve 42.

Specifically, to disengage the cap 84 from the valve 30, sufficient torque must be imparted to the cap 84 to strip to ratchet threads 86. Consequently, once the cap 84 has been removed from the valve 30, it cannot be reengaged with the valve 30. Thus, a missing or stripped cap 84 indicates that the cap 84 has been tampered with. It is to be understood that if desired, a new cap (not shown) that is in all essential respects identical to the cap 84 can be engaged with the valve 30, although the new cap can be a different color than the cap 84.

In the operation of the bag 10, reference is made to FIG. 1. With the bag 10 initially full of fluid to be infused into the patient 14, the valves 30, 42 are closed to prevent fluid flow through the ports 28, 36. In other words, the valve members 54, 72 are biased into their normally closed configurations. Also, the membrane within the conventional port 24 prevents fluid flow through the conventional port 24.

A path for fluid communication can be established through any one of the ports 24, 28, 36 by advancing an appropriate connector into the particular port. For example, fluid 12 from the bag 10 can be infused into the patient 14 by advancing a blunt spike (not shown) into the spikeless/ needleless port 28. Alternatively, fluid can be added to or extracted from the bag 10 by advancing the end 34 of the needleless syringe 32 into the port 28 and operating the plunger of the syringe 32 to inject fluid into the bag 10.

More particularly, as described above, the needleless syringe 32 is sufficiently advanced into the spikeless/ needleless port 28 (and the valve 30) to open the valve 30. Fluid 12 can then be injected into or extracted from the IV bag 10 through the spikeless/needleless port 28.

Similarly, the conventional spike 22 can be advanced into the conventional port 24 until the spike 22 pierces the membrane within the port 24. This establishes a path for fluid flow through the port 24, spike 22 and IV line 16 into the patient 14. This fluid flow can be effected by gravity drain or by engaging a peristaltic pump (not shown) with the IV line 16 and pumping fluid 12 into the patient 14.

Further, fluid can be injected or extracted from the IV bag 10 by engaging a needleless syringe with the belly button port 36 and appropriately operating the plunger of the syringe. More specifically, using the belly button port 36 as an example, the connector portion of the syringe can be advanced into the valve 42 to open the valve 42, and the plunger of the syringe then manipulated as appropriate to infuse or extract fluid into the bag 10. The skilled artisan will appreciate that the belly button port 36 can be used as another site to piggy back a container using a Luer fitting.

When it is no longer necessary to infuse fluid into the bag 10 through the spikeless/needleless port 28, the needleless syringe 32 is simply retracted from the spikeless/needleless port 28. This causes the resilient valve member 54 to resume its normally closed position to thereby block fluid flow through the spikeless/needleless port 28. Also, after fluid has been infused or extracted as appropriate from the bag 10 through the belly button port 36, the needleless syringe is simply retracted from the valve 42. This causes the resilient valve member 72 to resume its normally closed configuration, thereby preventing fluid flow through the bellow button port 36. FIG. 1A shows that a glass vial 200 can have a needleless port 202. A valve 204 which is in all essential respects identical to the valve 30 can be positioned in the port 202, to selectively establish a needleless connector through which fluid can pass into or out of the vial 200.

Now referring to FIGS. 5–11, several embodiments of liquid medicament bags in accordance with the present invention are shown. FIG. 5 shows that a liquid medicament bag 300 has a first multi-laminate side 302, a second multi-laminate side 304, and a seam 306 that is established at the juncture of the sides 302, 304. Thus, the sides 302, 304 with seam 306 establish a container of the type well-known in the art for holding, e.g., liquid medicament, cell culture, and other biotech fluids. The skilled artisan will accordingly appreciate that the material and thickness of the laminated layers are selected for strength, puncture resistance, gas permeability, and compatibility with the fluid contained in the bag 300. For example, FIG. 6 shows that the side 302 has two layers 302a, 302b. It is to be appreciated that the side 302 can have additional layers, if desired.

A rigid plastic valve assembly 308 is fixedly positioned on the seam 306 during manufacture by means well-known in the art, e.g., by rf sealing, spin welding, or ultrasonic welding, and the sides 302, 304 of the bag 300 are likewise connected, as indicated by a bond line 303. The assembly 308 in the perspective view shown has a catenary shape when looked at from above.

FIGS. 6 and 7 show that the valve assembly 308 is "H"-shaped in transverse cross-section, and has first and second openings 310, 312 which are established by flanges 310a, 310b. As shown, the flanges 310a, 310b are bonded to the sides 304, 302, respectively, of the bag 300. A first reflex valve 314 is positioned in the first opening 310 and a second reflex valve 316 is positioned in the second opening 312.

The first valve 314 is in all essential respects identical in construction to the valve 30 valve member disclosed above, except that the first valve 314 has grooves 315 formed in place of the protrusions 42a shown in FIGS. 2A and 2B. It is to be understood that the grooves 315 fulfill the same function as the protrusions 42a, i.e., the grooves 315 prevent a vacuum lock from being established between a valve member 317 and a valve body 319.

As shown best in FIG. 7, the second valve 316 also is identical to the valve 30, except that the second valve 316 has a male valve element 318. More particularly, the male valve element 318 has a cylindrical skirt 320 and a contact surface, preferably a shaped head 322 which extends radially outwardly from the skirt 320. Alternatively, the valve element 318 can have a non-rounded shape.

As shown, the second valve 316 is configured as a male luer fitting. Consequently, a female luer fitting 324 (FIG. 8) can be engaged with the valve 316 such that a tapered inner surface 326 of the female luer fitting 324 urges against the head 322 to move the second valve 316 to the open configuration.

While FIGS. 6 and 7 show a valve assembly 308 having two valves 314, 316 positioned therein, it is to be understood that the assembly 308 can have one or more openings, and that one or more of the openings can have a piercable membrane positioned therein, if desired. It is to be further understood that the male valve 316 can be used in place of the valves previously valve member losed, e.g., the male valve 316 can be used in place of the valve 30 shown in FIGS. 2A and 2B.

Figure 9:
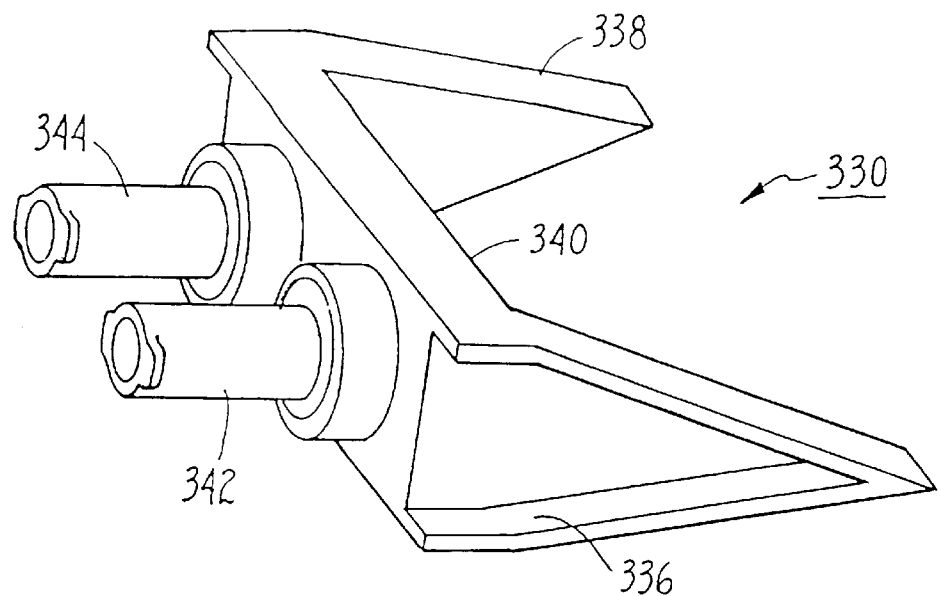
FIG. 9 is a perspective view of an alternate embodiment of the valve assembly for the liquid medicament bag of the present invention.

FIG. 9 shows that a valve assembly, generally designated 330, can have a configuration familiarly referred to as a "wedge" configuration. Specifically, in the view shown in FIG. 9, two engagement flanges 336, 338 depend downwardly from a bottom surface 340 of the assembly 330. It is to be understood that in accordance with the present invention, the flanges 336, 338 are positioned between the sides of a liquid medicament bag, i.e., in the seam of the bag, and are connected thereto by means well-known in the art. Like the valve assembly 308 shown in FIGS. 5–8, the valve assembly 330 has two or more reflex valves 342, 344 disposed in respective openings formed by the assembly 330.

Figure 10:
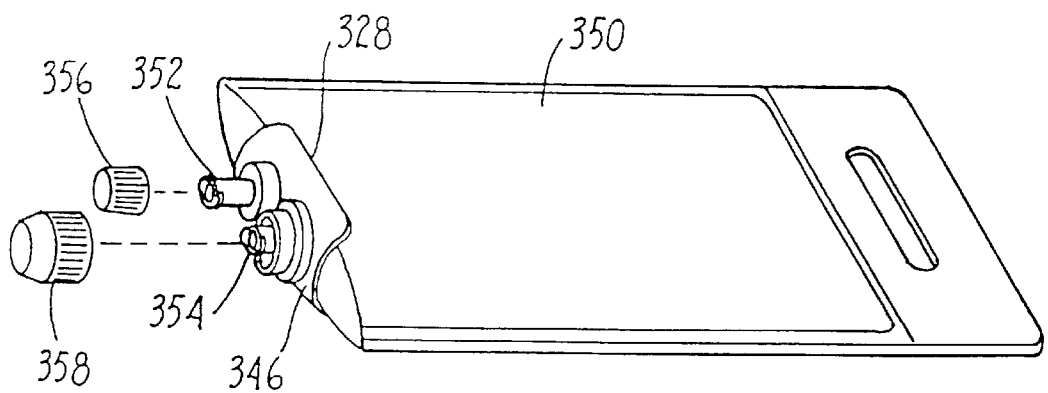
FIG. 10 is a perspective view of another alternate embodiment of the liquid medicament bag of the present invention, with the tamper-resistant caps shown in an exploded relationship with their respective valves.

FIG. 10 shows that a valve assembly 346 has a gently curved saddle shape bottom surface 348 for conforming to a bag 350. The assembly 346 is and attached to the bag 350 by means well-known in the art, e.g., solvent bonding, rf sealing, heat staking, or ultrasonic welding. Like the assemblies 308, 330 shown in FIGS. 5–9, the assembly 346 shown in FIG. 10 has two or more valves 352, 354. Also, each valve 352, 354 can have a respective tamper-resistant cap 356, 358 which is configured to engage a luer fitting. The caps 356, 358 can have a well-known configuration for resisting tampering, e.g., the caps 356, 358 can have plastic ratchet threads which strip during removal of the cap 356, 358 from its associated valve 352, 354.

Figure 11:
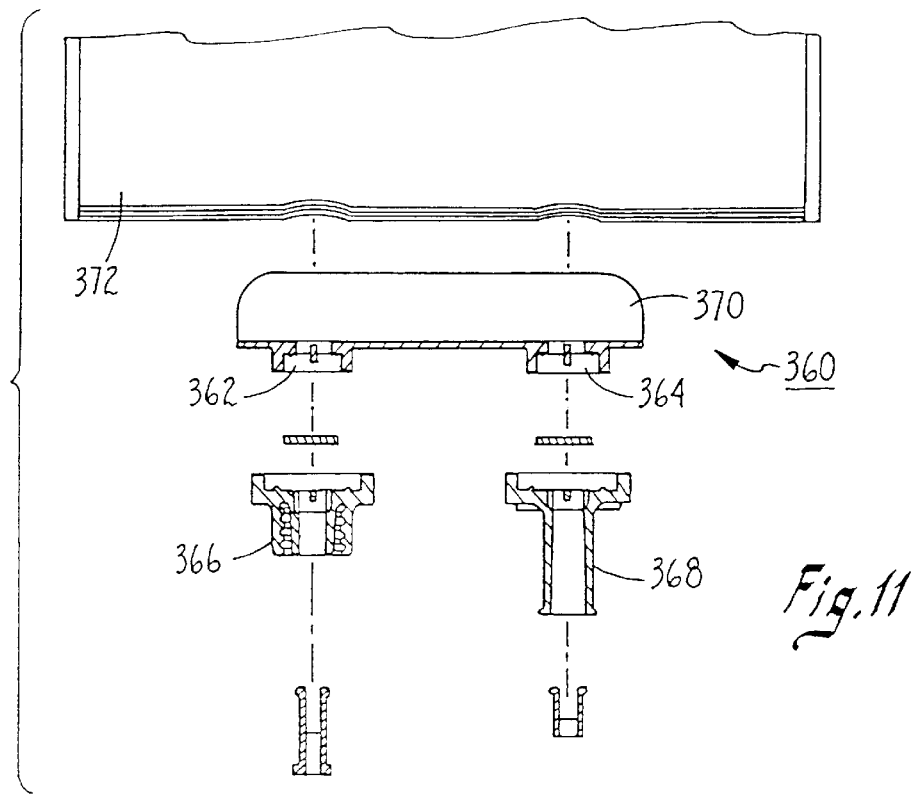
FIG. 11 is an exploded cross-sectional view of yet another alternate embodiment of the liquid medicament bag of the present invention.

FIG. 11 shows a valve assembly, generally designated 360, which has a socalled boat shape, and is accordingly referred to in the art familiarly as a "boat". The assembly 360 also has two openings 362, 364 and two valves 366, 368 respectively positioned in the openings 362, 364. The Valves 366, 368 can be female or male valves. In the embodiment shown, th& valve 366 is a male valve configured like the valve 316 shown in FIGS. 7 and 8, while the valve 368 is a female valve configured like the valve 30 shown in FIGS. 2A and 2B.

As can be appreciated in reference to FIG. 11, the assembly 360 has a hull surface 370 which is generally shaped like the gently rounded hull of a boat, and which consequently can be positioned between the juncture of two sides of a bag 372, and then attached to the bag by means well-known in the art. In other words, the hull surface 370 of the assembly 360 can be positioned in the seam of a liquid medicament bag.

In addition to the openings valve member discussed above, the assemblies 308, 330, 360 can have additional openings (not shown) which can be blocked by respective reflex valves or by pierceable membranes.

Figure 12:
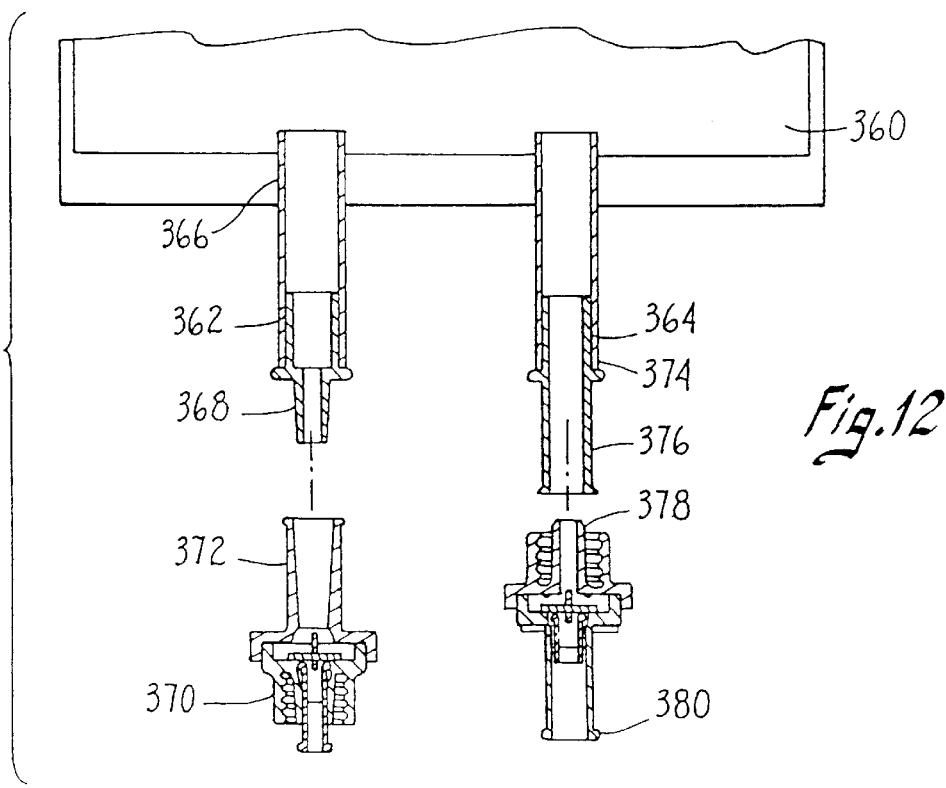
FIG. 12 is an exploded cross-sectional view of still another alternate embodiment of the liquid medicament bag of the present invention, with portions broken away, showing a valve of the present invention connected to a medicament bag by a luer fitting.
Figure 13:
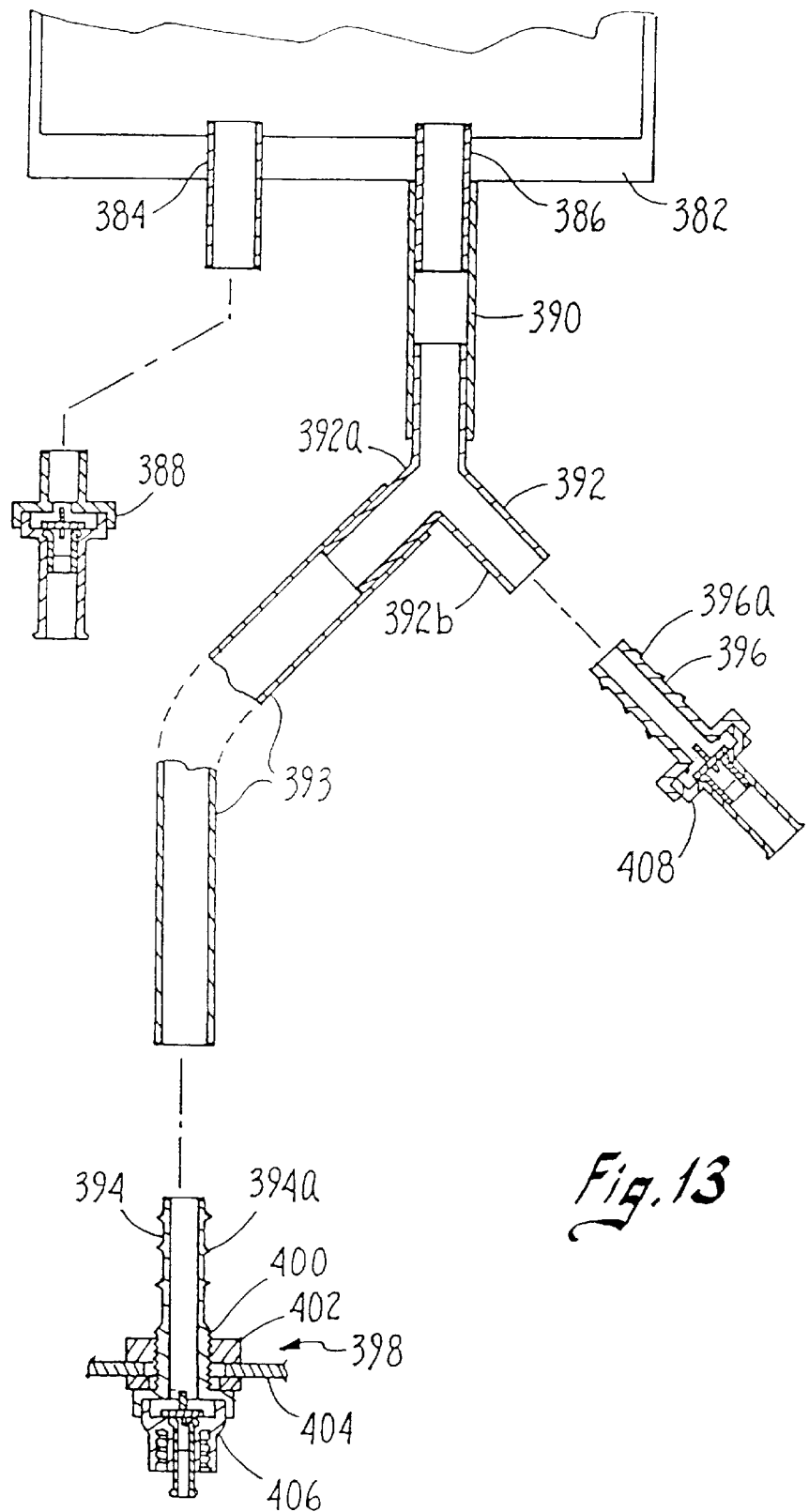
FIG. 13 is an exploded cross-sectional view of another alternate embodiment of the liquid medicament bag of the present invention, with portions broken away, showing a valve of the present invention connected to a medicament bag by a tubular connector.

FIGS. 12 and 13 show multi-layer medicament bags having multiple individual tubular connectors for receiving associated valves. More specifically, FIG. 12 shows a bag 361 which has a first tubular connector 363 and a second tubular connector 365. The first tubular connector 363 includes a hollow cylindrical tube 367 which is bonded to the bag 360 by means well-known in the art.

A hollow male luer connector 369 is closely received in the tube 366, and a female luer fitting 373 can be engaged with the male luer connector 369. A valve 371 which is in all essential respects identical to the valve 316 shown in FIG. 7 is bonded to the female luer fitting 373.

Likewise, the second tubular connector 365 includes a hollow cylindrical tube 374 which is bonded to the bag 361 by means well-known in the art. A hollow female luer connector 376 is closely received in the tube 374, and a male luer fitting 378 can be engaged with the female luer connector 376. A valve 380 which is in all essential respects identical to the valve 314 shown in FIG. 6 is bonded to the male luer fitting 378. IV lines or other components, e.g., spikes and drip chambers (not shown) having luer fittings can be engaged with the valves 371, 380 to selectively establish fluid flow through the connectors 363, 365 in accordance with the principles set forth above.

FIG. 13 shows that a multi-layer medicament bag 382 has a plurality of resilient plastic tubular connectors 384, 386. The connector 384 can closely receive a valve 388 which is in all essential respects identical to the valve 28 shown in FIGS. 2A and 2B. If desired, the valve 388 can be bonded to the connector 384.

FIG. 13 also shows that an intermediate connector tube 390 can be bonded to the connector 386, and a hollow Y-fitting 392 in turn bonded to the intermediate connector tube 390. If desired, an extender tube 393 can be connected to a first leg tube 392a of the Y-fitting 392, and a first luer bulkhead fitting 394 can be advanced into the extender tube 393. A second luer bulkhead fitting 396 can be advanced into a second leg tube 392b of the Y-fitting 392 or extension tubes (not shown) that are connected to the second leg tube 392b.

Each of the luer bulkhead fittings 394, 396 has respective ratchet rings 394a, 396a which are configured as shown for permitting the luer bulkhead fittings 394, 396 to be advanced into their respective tubes 393, 392b, and for preventing the luer bulkhead fittings 394, 396 from being easily retracted from their respective tubes 393, 392b. If desired, the luer bulkhead fitting 394 can also include a locking ring assembly, generally designated 398, which includes a threaded body 400, a locking ring 402 threadably engaged with the body 400, and a backing ring 404. The luer bulkhead fittings 394, 396 can advantageously be similar to any one of the luer bulkhead fittings made by Value Plastics, Inc. of Fort Collins, Colo.

A male reflex valve 406 which is in all essential respects identical to the valve 316 shown in FIG. 7 is bonded by means well-known in the art to the first bulkhead luer fitting 394. Likewise, a female reflex valve 408 which is in all essential respects identical to the valve 314 shown in FIG. 6 is bonded by means well-known in the art to the second bulkhead luer fitting 396. IV lines or other components, e.g., spikes and drip chambers (not shown) having luer fittings can be engaged with the valves 388, 406, 408 to selectively establish fluid flow through the connectors 384 and Y-leg tubes 392a, 392b (and extension tubes thereof, e.g., the tube 393) in accordance with the principles set forth above.

FIG. 14 shows a valve 450 which is a male reflux valve configured like the valve 316 shown in FIG. 7. Accordingly, the valve 450 includes a male Luer connector 452. In accordance with principles well known in the art, the male Luer connector 452 is formed with an outer frusto-conical wall 454 which tapers slightly radially inwardly from a proximal end 456 to a distal end 458 of the connector 452.

As shown, the valve 450 is bonded to an intravenous (IV) component 460. It is to be understood that the valve 450 can be attached to the component 460 by means well known in the art, e.g., solvent bonding, RF sealing, heat staking, spin welding, or sonic welding. As will be more fully valve member disclosed below, the IV component 460 can be any IV component for which it is desired to selectively establish fluid communication into or out of. For example, the IV component 460 can be an IV container such as a bag, or a syringe, spike, fluid line, drip chamber, connector fitting, filter, stopcock, Burette chamber, or adapter fitting. Consequently, the skilled artisan will appreciate that the valve 450 can be used in a large number of applications, including IV container devices and sets, enteral feeding, other biotechnology applications, other medical applications including cardiovascular, urology, anesthesiology and chemotherapy.

FIG. 15 shows a male reflux valve 462 which is bonded to a female Luer fitting 464. A fluid passageway 466 is established by the valve 462 and the female Luer fitting 464, and fluid communication through the fluid passageway 466 is selectively established by manipulating a male valve element 468 of the valve 462 as described previously. It is to be understood that the female Luer fitting 464 can include a female reflux valve as described previously.

FIG. 16 shows a male reflux valve 470 which is bonded to a connector 472, and the connector 472 has cylindrical walls 474, 476. The external walls 476 or the internal walls 474 of the connector 472 can in turn be bonded to another IV component. The reflux valve 470 selectively establishes fluid flow through the fluid passageway which is established by the connector 472.

FIG. 17 shows a male reflux valve 478 which is bonded to a check valve 480, and the check valve 480 is in turn bonded to an IV component 482. As shown, the male reflux valve includes a male valve element 484, a reflux disk 486, a support element 488 for supporting the reflux disk 486 in the center thereof, and a retainer element 490. The check valve 480 includes a check valve body 492 and a check valve disk 494. Also, a check valve support element 496 is provided for supporting the check valve disk 494 in the center thereof. It can be appreciated in reference to FIG. 17 that the support element 488 functions as a retainer element for the check valve disk 494.

It will be further appreciated that the check valve disk 494 permits fluid flow through a fluid passageway 498 only in the direction indicated by the arrow 500 and substantially prevents fluid flow in a direction opposite the arrow 500. This is true regardless of whether the male valve element 484 has been urged into the reflux disk 486 to form the disk. Accordingly, the combination of structure shown in FIG. 17 results in a modified check valve in which fluid flow only in the direction of the arrow 500 is permitted, only when the male valve element 484 is urged against the reflux disk 486. It is to be understood that in some applications, the male reflux valve 478 can be replaced by a female reflux valve (not shown).

FIG. 18 shows a male reflux valve 502 which is engaged with a barbed connector 504 that is formed with a plurality of frusto-conical shaped barbs 506, with the barbs being configured for securely engaging the lumen of another IV component (not shown), such as an IV line. Other barb shapes may also be used. The male reflux valve 502, in accordance with the valve member discussion above, selectively establishes fluid communication through a cylindrical passageway 508 which is established by the barbed connector 504.

FIG. 19 shows a male reflux valve 510 which is connected to a stepped connector 512 having a plurality of steps 514, with the steps being configured for securely engaging the lumen of another IV component (not shown), such as an IV line. The reflux valve 510 selectively establishes fluid flow through a cylindrical fluid passageway 516 which is established by the stepped connector 512. It is to be understood that the connector 512 can have a continuously tapered outer wall instead of the steps shown.

FIG. 20 shows a male reflux valve, generally designated 518, which includes a male valve element or female valve element 520 and a valve body 522. As shown, the valve element 520 includes a contact flange 524 defining a flat contact surface 526 and a body surface 528 that is opposed to the contact surface 526. As shown in FIG. 20, the body surface 528 defines an angle α relative to the contact surface 526. More specifically, the body surface 528 defines an angle α relative to the contact surface 526 of between about 5° and 75°.

Likewise, the valve body 522 is formed with an abutment surface 530 which is generally parallel to the body surface 528 of the contact flange 524. It is to be understood that the abutment surface 530 and body surface 528 interlock with each other to more securely hold the valve element 520 within the valve body 522.

FIG. 21 shows a male reflux valve 534 which is connected to a connector 536 for selectively establishing fluid flow through a cylindrical fluid passageway 538 defined by the connector 536. As shown, the connector 536 has a tapered segment 540 and a threaded segment 542 for engaging a complementarily threaded IV component.

FIG. 22 shows a male reflux valve 544 which is disposed in a port 546 of a so-called "T"-site connector 548. The T-site connector 548 defines a main fluid passageway 550 and a secondary fluid passageway 552, and the male reflux valve 544 can be manipulated as described above to selectively permit fluid communication through the secondary fluid passageway 552 of the T-site connector 548.

FIG. 23 shows a male reflux valve 554 which is disposed in a port 556 of a so-called "Y"-site connector 558. As shown, the Y-site connector 558 defines a main cylindrical fluid passageway 560 and a secondary fluid passageway 562. The valve 554 can be operated as valve member disclosed above to selectively block fluid communication through the secondary passageway 562 of the Y-site connector 558.

FIG. 24 is an exploded view of a male reflux valve, generally designated 564, and a female reflux valve, generally designated 566. As valve member disclosed above, the male reflux valve 564 includes a valve body 568 which is configured as a male Luer fitting, while the female reflux valve 566 includes a valve body 570 generally configured as a female Luer fitting.

Each of the valves 564, 566 includes its own disk, represented by the single disk 572 shown in FIG. 24. Either of the valves 564, 566 can be engaged in either one of the ports 574, 576 of respective syringes 578, 580. The skilled artisan will appreciate in reference to FIG. 24 that the syringe 578 is a shaft-style syringe and accordingly includes a shaft 582 connected to a proximal plunger 583. On the other hand, the syringe 580 is a syringe of the style made by Smith and Nephew, and accordingly has no shaft connected to the plunger. In accordance with principles valve member disclosed above, fluid communication through the ports 574, 576 of the syringes 578, 580 can be selectively established by either one of the valves 564, 566.

Figure 25:
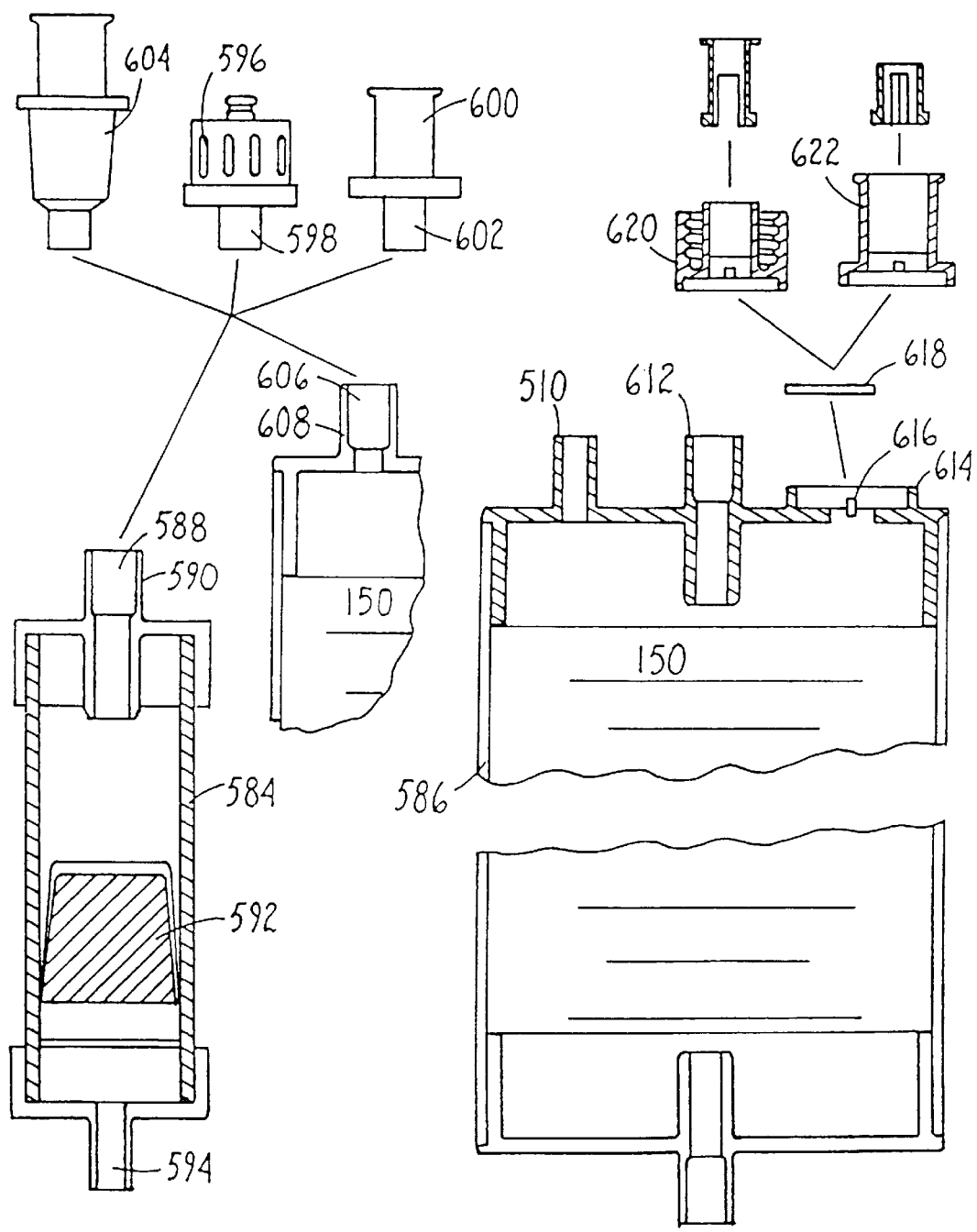
FIG. 25 is an exploded partial cross-sectional view of various reflux valves in combination with a drip chamber and a Burette chamber.

FIG. 25 shows a plurality of valving arrangements which can be used to selectively block fluid communication through the ports of a drip chamber 584 and a Burette chamber 586. More specifically, the drip chamber 584 has a port 588 which is established by an outwardly protruding cylindrical wall 590. The drip chamber 584 further includes a cone or sock filter 592 which covers an outlet port 594. It is to be understood that the filter 592 can have other configurations known in the art, e.g. as shown in FIG. 25.

The inlet port 588 of the drip chamber 584 can receive one of a plurality of valves for selectively blocking fluid communication through the port 588. More specifically, a first male reflux valve 596 can have a bonding segment 598 which is bonded to the walls 590 of the inlet port 588. It is to be understood that the male reflux valve 596, like the other male reflux valves valve member disclosed herein, is substantially identical in configuration to the reflux valve 316 shown in FIG. 7.

Alternatively, a first female reflux valve 600 having an engagement segment 602 can be disposed in the inlet port 588 of the syringe 584, with the engagement segment 602 being bonded to the walls 590 of the inlet port 588. It is to be understood that the first female reflux valve 600 is substantially identical in configuration to the other female reflux valves previously described, e.g. the valve 30 shown in FIG. 1. Furthermore, a second female reflux valve 604 can be disposed in the port 588 of the drip chamber 584 to selectively establish fluid communication through the inlet port 588. The second female reflux valve 604 may be configured differently than the first female valve 600, e.g. the second female valve 604 may be one of the IV valves made by Clavey or Halkey-Roberts.

Still referring to FIG. 25, the Burette chamber 586 has a first inlet port 606 which is defined by an outwardly protruding cylindrical wall 608. It can be appreciated in reference to FIG. 25 that any one of the valves 596, 600, 604 may be disposed in the first inlet port 606 of the Burette chamber 586 to selectively block fluid communication therethrough in accordance with principles valve member disclosed above. Furthermore, FIG. 25 shows that the Burette chamber 586 has second and third inlet ports 610, 612 and a fourth inlet port 614. As shown, the fourth inlet port 614 includes a support element 616, the function of which has been described previously in relation to supporting a deformable valve member of the present invention.

Accordingly, the support element 616 supports a deformable resilient disk 618 which can be the disk of a male reflux valve 620 or a female reflux valve 622 under the principles valve member disclosed previously. Thus, it will be understood that the fourth inlet port 614 of the Burette chamber 586 can be configured as a portion of the valve assembly for either one of the valves 620, 622.

Now referring to FIG. 26, a filter chamber, generally designated 624, has a first port 626, a second port 628, and a chamber 630 formed therebetween. As shown, the chamber 630 is catenary-shaped in cross-section. Also, a disk-shaped filter 632 is disposed in the catenary-shaped chamber 630.

A reflux valve in accordance to the present invention can be disposed in either one or both of the ports 626, 628. In the embodiment shown in FIG. 26, a male reflux valve 634 is disposed in the second port 628, while a female reflex valve 636 is disposed in the first fluid port 626. In accordance with the principles of the present invention valve member disclosed above, either one or both of the reflux valves 634, 636 may be operated to selectively establish fluid communication through its respective port 628, 626 and into the catenary-shaped chamber 630.

FIG. 27 shows an IV stopcock, generally designated 638. In accordance with principles well known in the art, the stopcock 638 includes a central fluid passageway that is covered by a cover plate 640, and an operating hand wheel 642. Additionally, the stopcock 638 can include at least two ports, and can include additional ports. In the embodiment shown in FIG. 27, the stopcock 638 includes first, second and third ports 644, 646, 648. A respective reflux valve is disposed in each one of the ports 644, 646, 648 to selectively establish fluid communication through the port. More particularly, a first female reflux valve 650 is disposed in the first port 644, a male reflux valve 652 is disposed in the second port 646, and a second female reflux valve 654 is disposed in the third port 648. The first and second female reflux valves 650, 654 are in all essential respects identical in configuration to the reflux valve 30 shown in FIG. 1, while the male reflux valve 652 is in all essential respects identical to the male reflux valve 316 shown in FIG. 7. It is to be further understood that one or more of the ports 644, 646, 648 may not include a reflux valve, and that for the embodiment shown in FIG. 27, i.e. a stopcock 638 having three ports, one of the ports will contain a male reflux valve while the remaining ports will contain female reflux valves.

Figure 28:
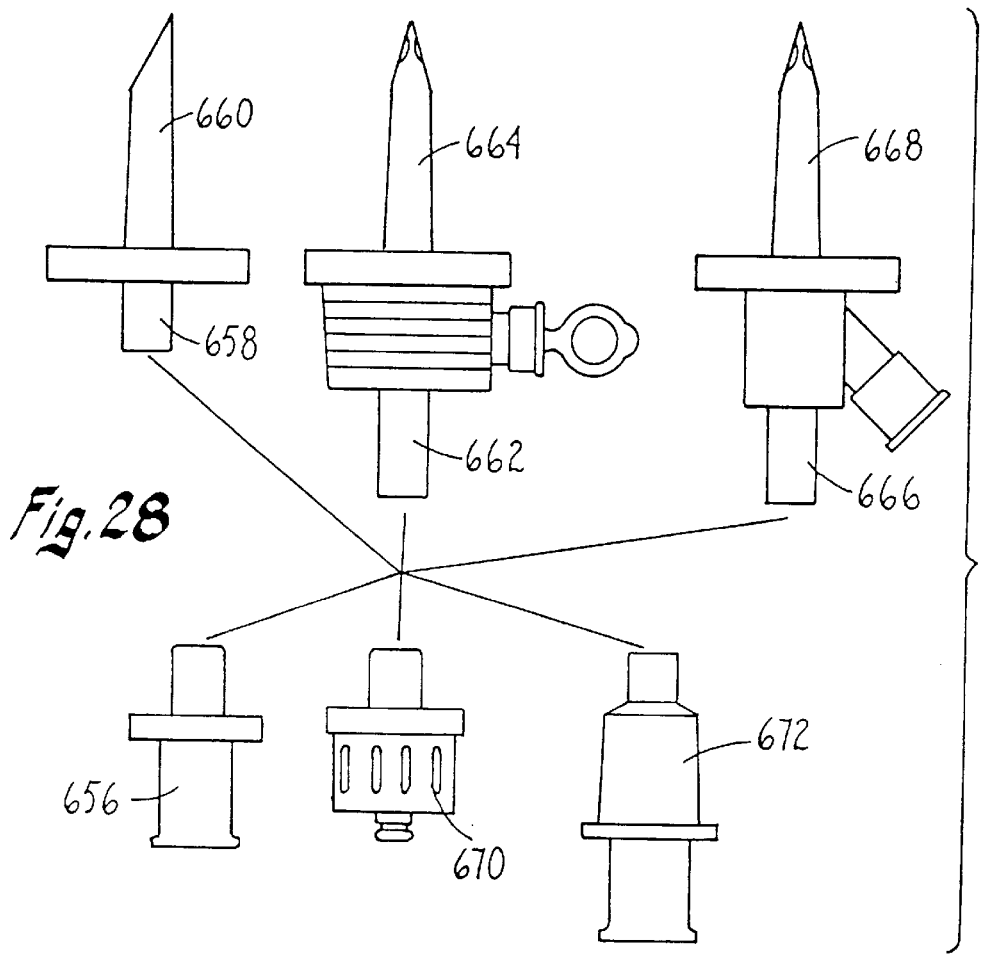
FIG. 28 is an exploded plan view of various reflux valves in operable engagement with various types of spikes.

Now referring to FIG. 28, the skilled artisan will appreciate that the reflux valves of the present invention can be disposed in various types of spikes for selectively establishing fluid communication through the spikes. More particularly, a first female reflux valve 656 can be disposed in an outlet port 658 of a nonvented spike 660. Also, the first female reflux valve 656 can be disposed in the outlet port 662 of a first vented spike 664. Moreover, the first female reflux valve 656 can be disposed in an outlet port 666 of a second type of vented spike 668. In accordance with the present invention, the first female reflux valve 656 is configured substantially identically to the reflux valve 30 shown in FIG. 1 and can be fixedly engaged in any one of the spikes 660, 664, 668 by means well known in the art valve member disclosed above.

Furthermore, a male reflux valve 670 which is in all essential respects identical in configuration to the reflux valve 316 shown in FIG. 7 can be engaged with any one of the outlet ports 658, 662, 666 of the respective spikes 660, 664, 668. Additionally, a second female reflux valve 672 can be engaged with any one of the ports 658, 662, 666 of the respective spikes 660, 664, 668. As intended by the present invention, the second female reflux valve 672 is substantially identical to the female reflux valve 604 shown in FIG. 25.

Figure 29:
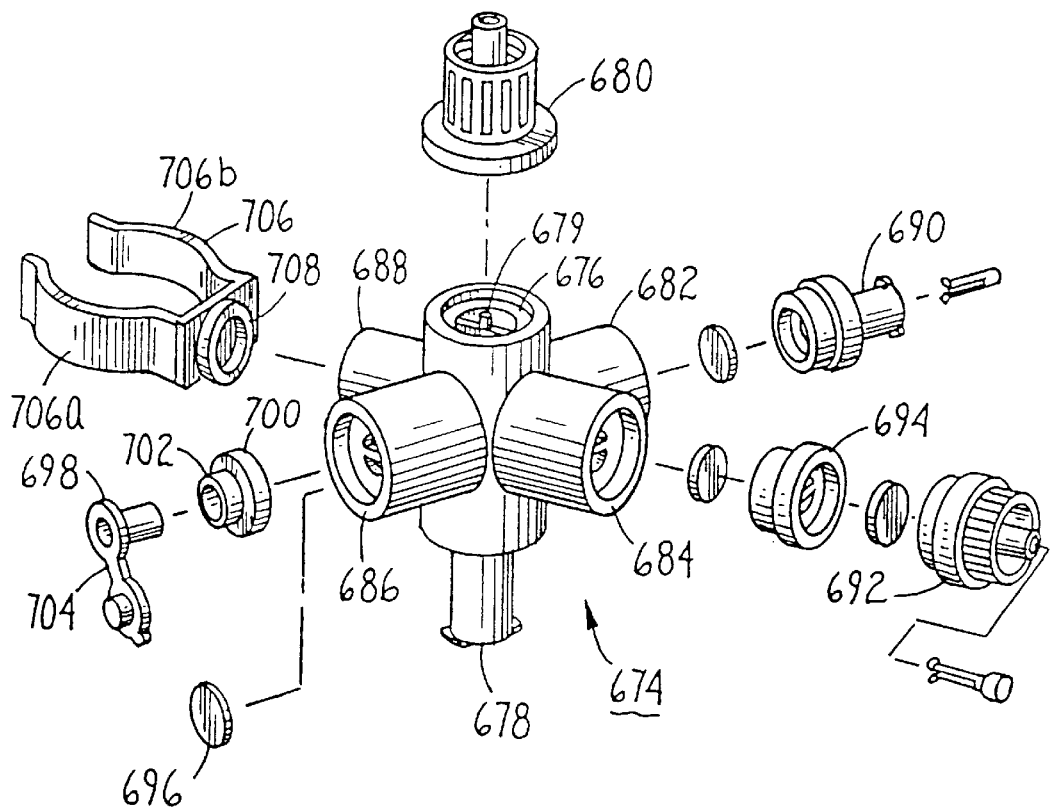
FIG. 29 is an exploded isometric view of a four-way valve with various associated components including Luer fittings with reflux valves.

Now referring to FIG. 29, a novel multiport IV valve of the present invention, generally designated 674, can be seen. As shown, the multiport valve 674 includes a first port 676 which is generally cylindrically shaped, and a second port 678 which is also generally cylindrically shaped and is configured as a female Luer fitting. As can be appreciated in reference to
FIG. 29, the first and second ports 676, 678 are coaxial and establish a main fluid passageway therebetween. A first male Luer valve 680 is fixedly engaged with the first port 676 for selectively blocking fluid communication therethrough.

FIG. 29 additionally shows that the multiport valve 674 includes third, fourth, fifth and sixth ports 682, 684, 686, 688, all of which are generally cylindrically shaped. As shown, the third and fifth ports 682, 686 are coaxial with each other. Likewise, the fourth and sixth ports 684, 688 are coaxial with each other. Each of the third through sixth ports 682, 684, 686, 688 defines a respective fluid pathway, and fluid communication through the fluid pathway can be selectively established or otherwise effected as valve member disclosed below.

For example, a female reflux valve 690 can be disposed in the third fluid port 682 for selectively establishing fluid communication through the port 682 and into the main fluid passageway 679 in accordance with principles valve member disclosed previously. Moreover, a combination male reflux valve-check valve 692, 694, which is substantially identical to the valve 478, 480 shown in FIG. 17, can be disposed in the fourth fluid inlet port 684 of the multiport valve 674. If desired, the male reflux valve 692 can be replaced with a female reflux valve (not shown) which is substantially identical to the female reflux valve 30 shown in FIG. 1.

Additionally, fluid communication through the fifth inlet port 686 can be permanently blocked if desired by bonding a plug 696 within the port 686 by means well known in the art. Alternatively, the fifth fluid inlet port 686 can hold a fluid filter, e.g. a filter 698. As shown, the filter 698 includes a filter element 700 having a membrane 702 through which air can pass. The filter 698 also includes a plug element 704 which engages filter element 700 and which holds the filter element 700 within the sixth fluid port 686.

Figure 30:
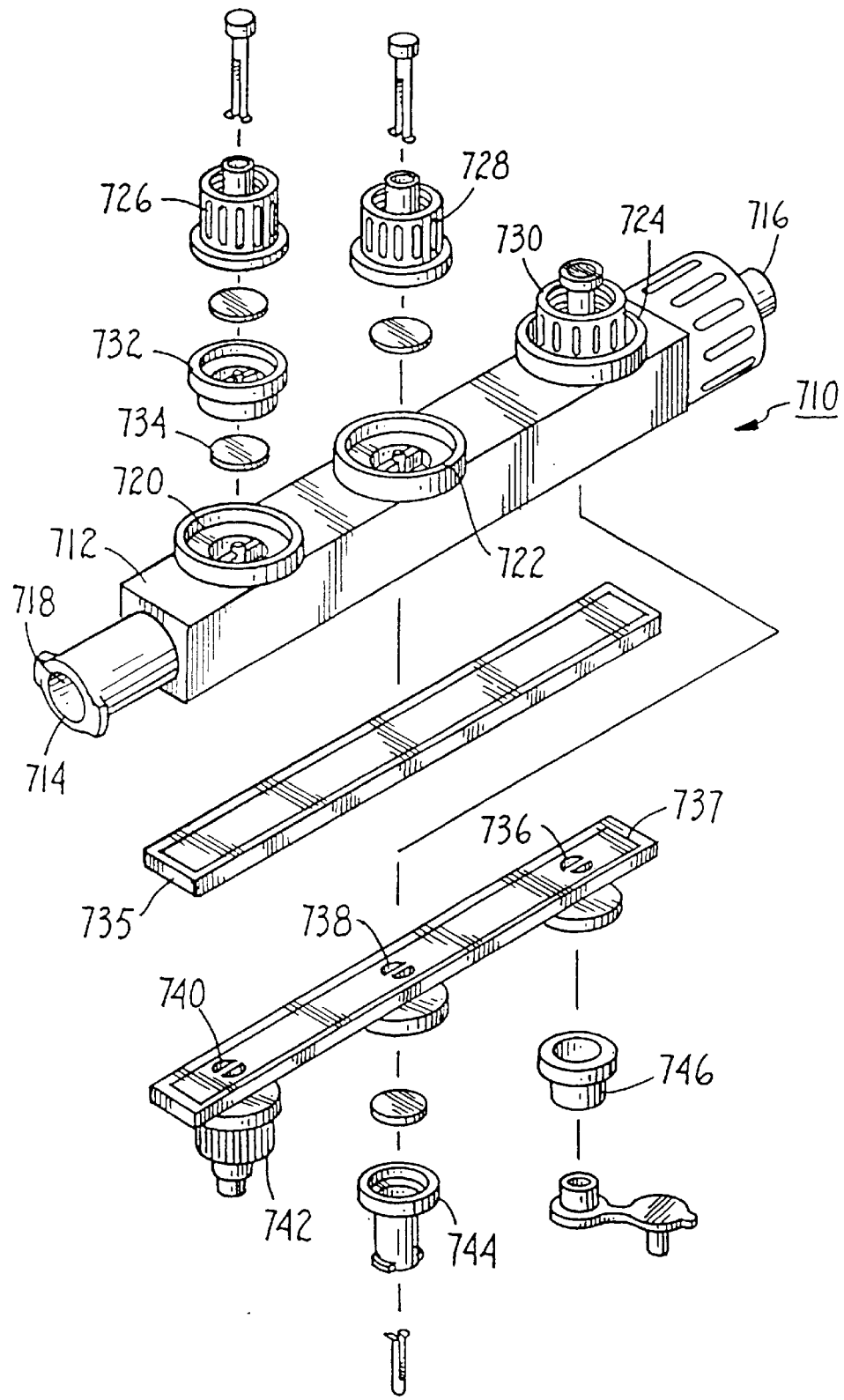
FIG. 30 is an exploded isometric view of an in-line multiport valve assembly.

Now referring to FIG. 30, an inline multiport valve is shown, generally shown 710. As shown, the valve 710 includes an elongated, generally parallelepiped-shaped valve body 712 that is formed with a fluid inlet port 714 and a fluid outlet port 716. The fluid inlet port 714 is configured as a female Luer fitting and the fluid outlet port 716 is configured as a male Luer fitting. A generally cylindrical main fluid passageway 718 is established through the valve body 712 between the ports 714, 716.

Additionally, the valve body 712 is formed with two to six fluid inlet ports. In the embodiment shown in FIG. 30, the valve body 712 includes first through third fluid inlet ports 720, 722, 724. One or more reflux valves may be positioned in the ports 720, 722, 724 to selectively establish fluid communication therethrough. More particularly, a first male reflux valve 726 is positioned in the first port 724, a second male reflux valve 728 is positioned in the second port 726, and a third male reflux valve 730 is positioned in the third port 724. The first male reflux valve 726 can include a check valve 732 having a deformable valve member 734 to establish a reflux-check valve like the structure shown in FIG. 17.

When the inline multiport valve 710 includes only three ports, a solid, continuous parallelepiped-shaped bottom plate 735 is rf sealed or ultrasonically welded to the valve body 712 opposite the first through third ports 720, 722, 724. On the other hand, the inline multiport valve 710 may include additional ports, in which case the bottom plate 735 is replaced with a port plate 737 which is formed with fourth through sixth ports 736, 738, 740. A male reflux valve 742 can be positioned in the sixth port 740, a female reflux valve 744 can be positioned in the fifth port 738, and a filter 746 which is similar to the filter 698 shown in FIG. 29 can be positioned in the fourth port 736. The fourth port 736 can include the mounting bracket, reflux valves, filter, plug, and check valve options shown in FIG. 29.

Figure 31:
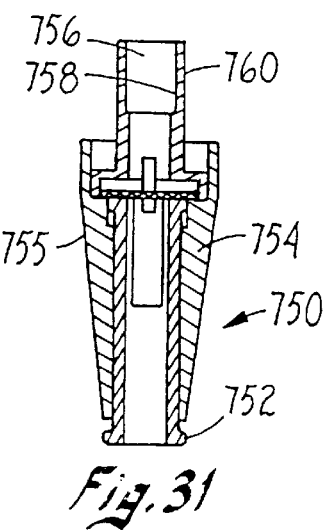
FIG. 31 is a cross-sectional view of a male reflux valve in operable engagement with a tapered adapter fitting.

FIG. 31 shows that a male reflux valve, generally designated 750, can include a male valve element 752 and a frusto-conical shaped valve body 754, which is formed with a tapered wall 755. It is to be understood that the valve body 754 is configured as an adapter fitting, e.g., a Luer catheter adapter, a 9/32 adapter, or 3/16 adapter, for interconnecting two IV components having inside diameters differing from each other.

The valve 750 has a port 756 defined by an inner cylindrical wall 758 which is surrounded by an outer cylindrical wall 760. Either of the walls 758, 760 can be bonded to an IV component (not shown) by means well-known in the art.

Figure 32:
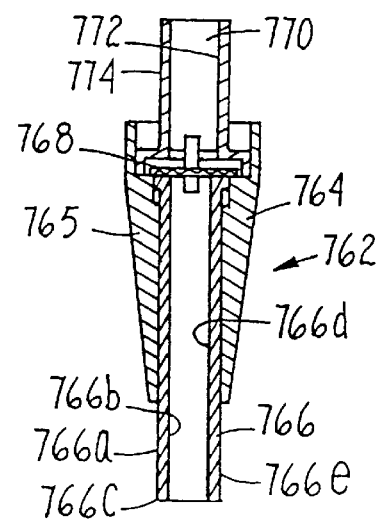
FIG. 32 is a cross-sectional view of a male reflux valve of the present invention in operable engagement with an enteral fitting.

FIG. 32 shows a valve, generally designated 762, having a frusto-conical shaped body 764 formed with a tapered wall 765 for configuring the valve 762 as an enteral feeding adapter. The valve 762 also includes a hollow cylindrical valve element 766 having an outer wall 766a which tapers toward an inner wall 766b near a distal end 766c of the element 766. For purposes of the present invention, the valve element 766 includes a skirt 766d disposed in the valve body 764 and an engagement surface 766e that extends beyond the fluid passageway established by the valve body 764. Also, the valve 762 includes a deformable resilient valve member 768, and the valve element 766 can be urged against the valve member 768 to deform the valve member and thereby permit fluid communication through the valve 762.

The valve 762 has a port 770 defined by an inner cylindrical wall 772 which is surrounded by an outer cylindrical wall 774. Either of the walls 772, 774 can be bonded to an IV component (not shown) by means well-known in the art.

While the particular needleless valve for use with intravenous infusion components as herein shown and described in detail is fully capable of attaining the objects stated above, it is to be understood that it is but the presently preferred embodiments of the present invention, and that the scope of the present invention is accordingly to be ignited by nothing other than the appended claims.

I claim:

1. An IV port, comprising:
   an IV container selected from the group of containers consisting of flexible IV bags and rigid IV container;
   at least one port body extending from the IV container;
   a valve body operably engaged within the port body, the valve body defining a fluid passageway for permitting fluid flow into and out of the IV container, the valve body being configured as a female luer fitting; and
   a valve member positioned in the valve body for selectively blocking fluid through the valve body,
   the valve member defining an outer periphery that is uninterrupted within the periphery, the valve member being disposed in the valve body and biased to a closed configuration, wherein a passageway for fluid communication is not established through the valve body,
   the valve member being movable to an open configuration when a mating component is engaged, wherein two-way fluid communication through the valve body is permitted.

2. The port of claim 1, wherein the port body is configured in the shape referred to as a "Wedge" port.

3. The port of claim 1, wherein the port body is configured in the shape referred to as a "Boat port".

4. The port of claim 1, wherein the port body is configured in the shape referred to as a "Saddle" port.

5. The port of claim 1, wherein the port body is configured in the shape referred to as a "Belly Button" port.

6. The port of claim 1, wherein the port body is configured as a check valve, in which a resilient valve member biased to the first configuration, wherein a passageway for fluid communication is not established through the valve body, the member being deformable to a second configuration, wherein fluid communication through the body is permitted.

7. The port of claim 1, wherein the valve body has a continuous smooth outer surface defining a periphery, the valve body being in contact with the IV container entirely around the periphery to facilitate leak-free engagement between the bag and the valve body.

8. The port of claim 7, wherein the IV container is a bag, and the port further comprises a tube disposed in the bag, the valve body being received in the tube for facilitating leak-free engagement between the bag and the valve body.

9. A port comprising:
   a container selected from the group of containers consisting of flexible IV bags and rigid IV containers;
   at least one port body extending from the IV container, the port body configured as a wedge port, boat port, or a saddle port;
   a valve body operably engaged within the port body, the valve body defining a fluid passageway for permitting fluid flow into and out of the IV container, the valve body being configured as a luer fitting;
   a valve member positioned in the valve body for selecting blocking fluid through the valve body, the valve member defining an outer periphery, the valve member being disposed in the valve body and biased to a closed configuration, wherein a passageway for fluid communication is not established through the valve body, the valve member being movable to an open configuration when the leur is engaged, wherein two-way fluid communication through the valve body is permitted.

10. The port of claim 9 wherein the luer is configured as a female luer.

11. The port of claim 9 wherein the luer is configured as a male luer, with a male valve element disposed in the valve body and defining an engagement surface extending outwardly beyond the valve body for contacting a connector to cause the valve element to move the valve member to an open configuration.

12. A port comprising:

a container selected from the group of containers consisting of flexible IV bags and rigid IV containers;

a valve body defining a port for permitting fluid flow into and out of the IV container, the valve body being configured as a luer fitting;

at least one port body configured as a belly button port;

a valve member positioned in the valve body for selectively blocking fluid flow through the valve body, the valve member defining an outer periphery that is uninterrupted within the periphery, the valve member being disposed in the valve body and biased to a closed configuration, wherein a passageway for fluid communication is not established through the valve body, the valve member being movable to an open configuration when the luer is engaged, wherein two-way fluid communication through the valve body is permitted.

13. A port according to claim 12, wherein the luer is configured as a male luer.

* * * * *